United States Patent
Osypka

[11] Patent Number: 5,999,835
[45] Date of Patent: Dec. 7, 1999

[54] CONNECTION ELEMENT FOR AN OUTER END PIECE OF A SURGICAL ELECTRODE

[75] Inventor: Peter Osypka, Grenzach-Wyhlen, Germany

[73] Assignee: Sulzer Osypka GmbH, Grenzach-Wyhlen, Germany

[21] Appl. No.: 08/884,258

[22] Filed: Jun. 27, 1997

[30] Foreign Application Priority Data

Aug. 6, 1996 [EP] European Pat. Off. .............. 96810517

[51] Int. Cl.$^6$ ........................................................ A61B 5/04
[52] U.S. Cl. ........................ 600/393; 600/391; 600/394
[58] Field of Search .................. 606/32, 35; 600/372, 600/374, 391, 393, 394, 392

[56] References Cited

U.S. PATENT DOCUMENTS

| | | | |
|---|---|---|---|
| 3,606,881 | 9/1971 | Woodson | 600/392 |
| 3,960,141 | 6/1976 | Bolduc . | |
| 4,097,104 | 6/1978 | Furey et al. | 600/393 |
| 5,427,243 | 6/1995 | Roshdy . | |

FOREIGN PATENT DOCUMENTS

| | | |
|---|---|---|
| 2 291 499 | 6/1976 | France . |
| 2 300 580 | 9/1976 | France . |

*Primary Examiner*—Michael Buiz
*Assistant Examiner*—Julian W. Woo
*Attorney, Agent, or Firm*—Townsend and Townsend and Crew LLP

[57] ABSTRACT

The connection element for an outer end piece of a surgical electrode is provided for application for the surface of the body of a heart patient. It provides a mechanical and an electrical connection between the outer end piece and a connection socket. It is advantageous to use one or a plurality of electrodes for the temporary monitoring and/or stimulation of the heart activity. One indifferent electrode arranged on the surface of the body, which is preferably mounted on a baseplate of the connection element, is associated with the or each unipolar electrode.

15 Claims, 2 Drawing Sheets

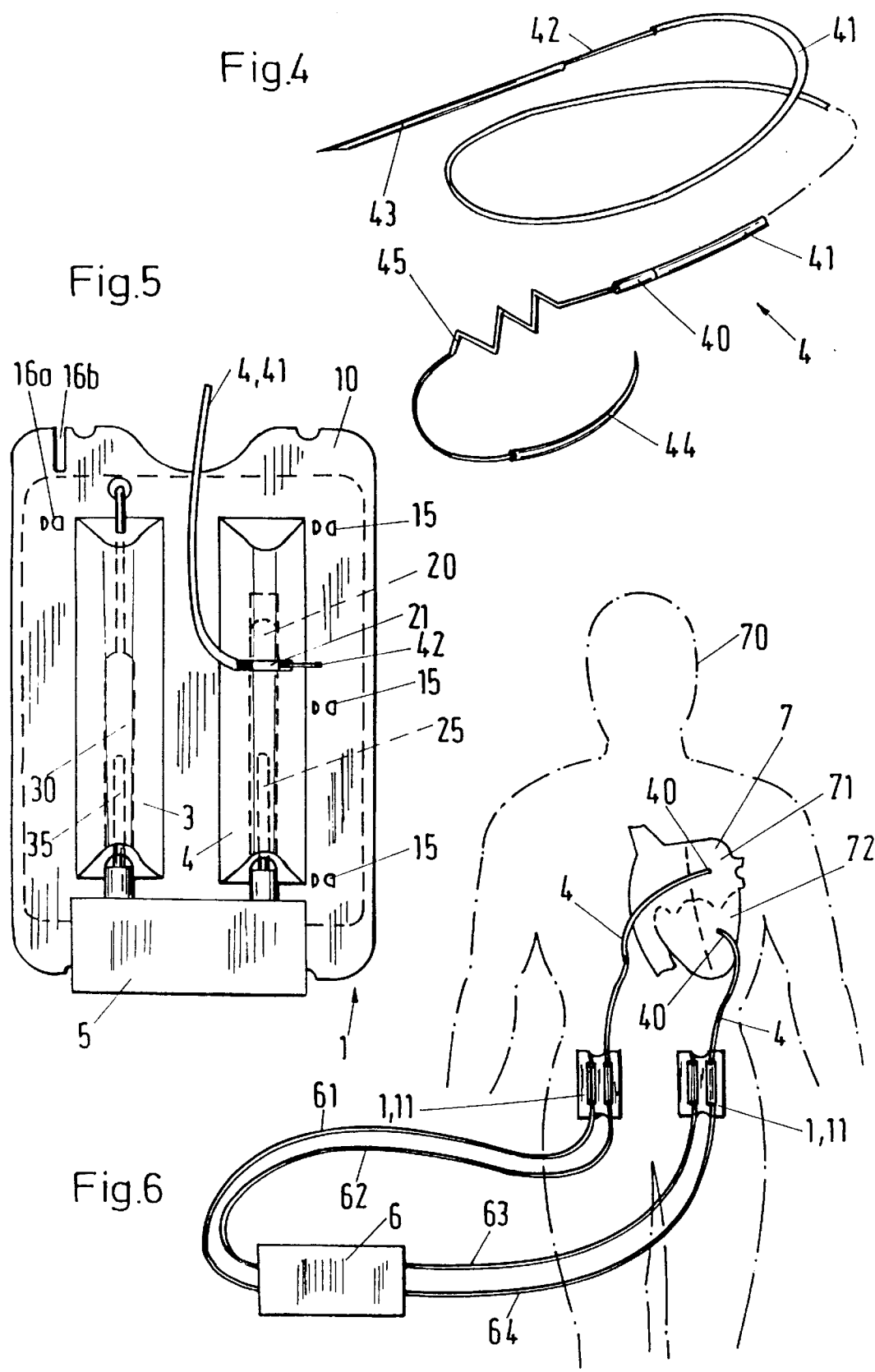

CONNECTION ELEMENT FOR AN OUTER END PIECE OF A SURGICAL ELECTRODE

BACKGROUND OF THE INVENTION

The invention relates to a connection element for an outer end piece of a surgical electrode as well as to uses of connection elements of this kind.

A surgical electrode, which is also called a heart wire, is known from the European Patent Specification EP 0 159 540. The heart wire is used after a heart operation for the temporary monitoring and stimulation of the heart activity. It forms an insulated electrical connection between two uninsulated ends. The one end is anchored in the heart muscle. The other end—the outer end piece—is located outside the thorax, where it can be connected to an external pacemaker or ECG monitor.

When using unipolar electrodes only one heart wire is required in each case. As a rule, two unipolar electrodes are used, the one for the auricular region of the heart and the other for the ventricular region. An indifferent or neutral electrode which is arranged on the body of the patient is associated with each unipolar electrode. When long electrodes are used—up to the connection at the named equipment—the outer parts of the wires are wound up and secured to the abdomen of the patient with tape without any special measures being taken. If the electrodes are short (60 cm), extension cables must be used for the external stimulation, since the stimulator and the ECG monitor are not located on the patient but rather at a certain distance in the vicinity of the bed. A tangle of cables often results, which can lead to a confusion of the cables.

SUMMARY OF THE INVENTION

The object of the invention is thus to provide means which enable a reliable treatment of heart patients when surgical electrodes are used. With connection elements in accordance with the invention, each electrode can be connected to one of the connection sockets. These connection elements permit a clearly recognizable arrangement of the connection points, a rapid connection extension cables by plugging them together, and thus a secure as well as rapid connection to the stimulator and/or ECG monitor. Relatively short heart wires (with a length of about 60 cm) can be used, which enables a clear discrimination.

The connection element in accordance with the invention for an outer end piece of a surgical electrode is provided for application to the surface of the body of the patient. It comprises means with which a mechanical and an electrical connection can be produced between an outer end piece and a connection socket. It is advantageous to use one or a plurality of unipolar electrodes for the temporary monitoring and/or stimulation of the heart activity. An indifferent electrode arranged on the body surface, and preferably arranged on a base plate of the connection element, is associated with the or each unipolar electrode.

BRIEF DESCRIPTION OF THE DRAWINGS

FIG. 4 is a perspective view of a unipolar heart wire (surgical electrode), FIG. 5 is a plan view of a terminal with a heart wire connected, and FIG. 6 is an illustration of how two terminals are to be arranged on the heart patient.

DESCRIPTION OF THE PREFERRED EMBODIMENTS

Figure 1:
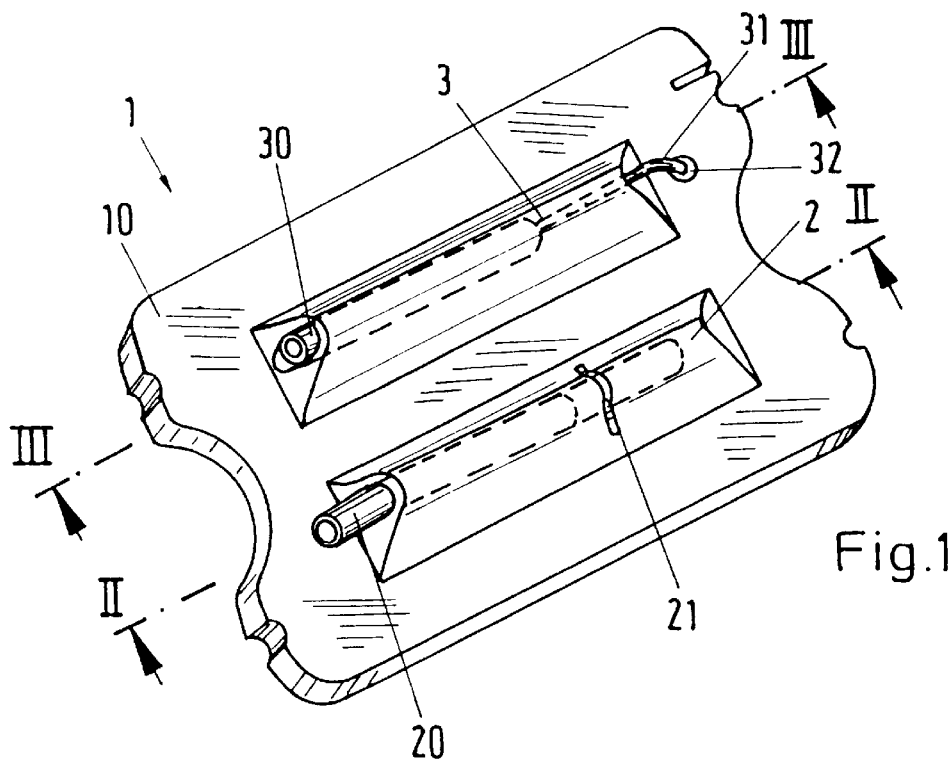
FIG. 1 is a perspective view of a connection element in accordance with the invention with two connection sockets—a so-called terminal.

The connection element in accordance with the invention or terminal 1 in FIG. 1 comprises the following parts: a baseplate 10, a connection point 2 for a heart wire 4 (see FIG. 4) and a connection socket 20, a connection point 3 for a connection socket 30 and an indifferent or neutral electrode (11, see FIG. 2) which is arranged on the underside of the baseplate 10 and is connected via a wire 31 and an element 32 to the socket 30. The connection point 2 has a slit-shaped insertion opening 21 for an outer end piece 42 of the heart wire 4.

At the underside of the baseplate 10, points can be provided which are coated with a skin-friendly, and where appropriate electrically conductive, adhesive and which permit a simple fastening of the terminal 1 to the patient.

Figure 2:
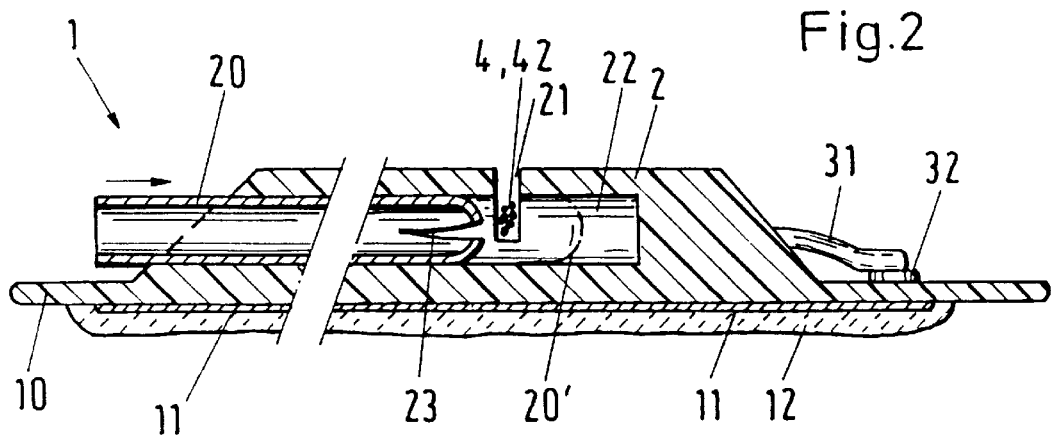
FIG. 2 is a section through the terminal of FIG. 1 along the line II—II.

The longitudinal section through the connection point 2 in FIG. 2 shows the movable connection socket or jack 20, which is displaceably guided in a channel 22 by its walls. The insertion opening 21 for the outer end piece 42 of the heart wire 4 (a braid) is arranged in a region of the channel 22 into which the socket 20 can be pushed. A mechanical and electrical connection between the outer end piece 42 and the connection socket 20 results through the insertion of the socket 20 and the wedging of the end piece 42 in a wedge-shaped slit 23 of the socket 20. The position of the socket 20 after the insertion is indicated by the chain-dotted line 20'. The connection between the heart wire and the socket 20 can also be produced in a different manner, for example by wedging of the end piece 42 between the socket 20 and the inner wall of the channel 22.

Figure 3:
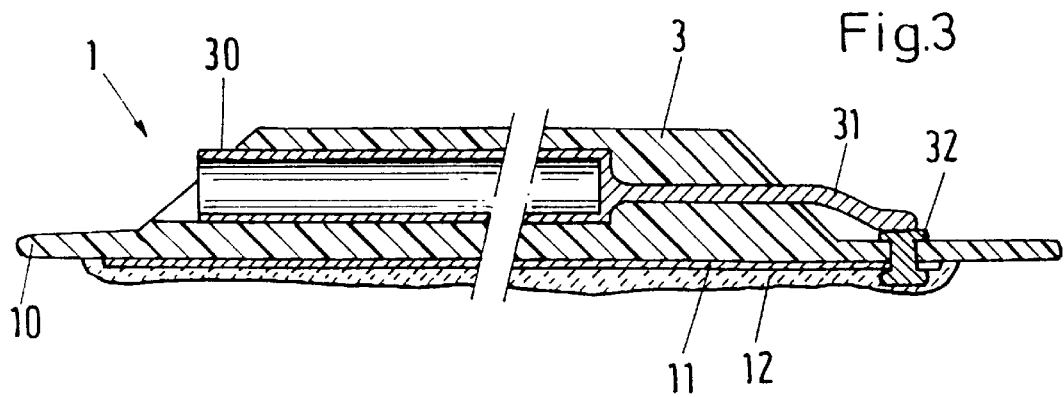
FIG. 3 is a second section through the terminal of FIG. 1 along the line III—III.

FIG. 3 shows the longitudinal section through the connection point 3 which connects the connection socket or jack 30 to the indifferent electrode 11 (wire 31, element 32). The electrode 11 is covered by an electrically conducting gel 12 which is provided for a trouble-free contact with the surface of the body of the patient and at the same time represents a skin-friendly adhesive.

The surgical electrode 4 or heart wire 4, which is shown in FIG. 4, is a known unipolar electrode and has the following parts: an insulated braid 41 with a length of for example 60 cm; a non-insulated braid piece which forms the outer end piece 42; a different or differential electrode 40 in the form of a sleeve of platinum by means of which an electrical contact to the heart muscle can be produced; and a zig-zag-shaped plastic thread 45 by means of which the heart wire 4 can be anchored in the heart muscle. A breast needle 43 and a heart needle 44 respectively are located at the two ends of the heart wire 4 as operational aids which can be severed off after being put to their intended use.

The terminal 1 of FIG. 5 is connected to the heart wire 4. A portable device 5 is connected directly to sockets 20 and 30. This device 5 is an ECG amplifier and remote controlled stimulator whose connection pins 25 and 35 are inserted instead of extension cables into the sockets 20 and 30 respectively. The stimulator can be externally programmed, for example via HF telemetry signals or by means of an infrared remote control.

The outline of the indifferent electrode 11 is shown in broken lines in FIG. 5. Furthermore, receiving elements 15 and 16a as well as 16b are shown which come into use when the terminal 1 is used as a part of the packaging for the surgical electrodes 4, namely as winding bodies for the electrode 4. The elements 15 are provided for the reception of the breast needle 43, the elements 16a, 16b for the reception of the heart needle 44. The baseplate 10, together with the connection points 2 and 3, forms a suitably formed winding body for the wire 41.

FIG. 6 shows the use of two connection elements 1 in accordance with the invention in the above described embodiment. The patient with the heart 7 is indicated by the chain dotted outline 70. This application relates to the temporary monitoring and/or stimulation of the heart activity with unipolar electrodes 4 and with indifferent electrodes 11 arranged on the surface of the body. Here the one electrode 4 is used for the treatment of the auricular region 71 of the heart 7 and the other for the treatment of the ventricular region 72. The terminals 1 are connected to a stimulator 6 via cables 61, 62, 63 and 64. The cables 61 and 63 each represent the connection to the indifferent electrodes 11, the cables 62 and 64 to the different electrodes 40. If portable devices 5 are used in accordance with FIG. 5, a synchronization is produced between the devices 5, for example by means of telemetry signals.

It is advantageous to manufacture the terminal of polyethylene as an injection molded plastic part. The sockets can be manufactured of brass with a subsequent gold plating.

I claim:

1. A connection element for an outer end piece of a surgical electrode for application to a surface of a body of a patient, the connection element comprising:
   an indifferent electrode which is configured to be arranged on the body of the patient;
   a first connection part electrically connected with the indifferent electrode, the first connection part including a first connection socket; and
   a second connection part for connecting with the outer end piece of the surgical electrode, the second connection part including a second connection socket which is electrically insulated from the first connection socket.

2. A connection element in accordance with claim 1 wherein the indifferent electrode is configured to be coupled to the body of the patient with a skin-friendly adhesive.

3. A connection element in accordance with claim 2 wherein the skin-friendly adhesive comprises an electrically conducting gel.

4. A connection element in accordance with claim 1 further comprising a baseplate which is coupled with the indifferent electrode, the first connection part, and the second connection part which is spaced from the first connection part, the baseplate being electrically nonconductive.

5. A connection element in accordance with claim 4 wherein the second connection socket is movably and displaceably guided in a channel in the baseplate.

6. A connection element in accordance with claim 5 wherein the channel is provided with an insertion opening for receiving the outer end piece of the surgical electrode into a region within the channel into which the second connection socket is to be inserted.

7. A connection element in accordance with claim 4 wherein the indifferent electrode is coupled to an underside of the baseplate, and the first connection part and second connection part are coupled to an upperside of the baseplate.

8. A connection element in accordance with claim 7 further comprising an electrically conductive member extending through the baseplate to connect the first connection part with the indifferent electrode.

9. A connection element in accordance with claim 8 wherein the electrically conductive member comprises an electrically conductive element disposed through an opening in the baseplate and connected with the indifferent electrode; and an electrically conductive wire connected between the electrically conductive element and the first connection part.

10. A connection element in accordance with claim 4 wherein the baseplate includes a plurality of receiving elements for receiving the surgical electrode and forming a winding body for the surgical electrode.

11. A connection element for a surgical electrode for application to a surface of a body of a patient, the connection element comprising:
   a baseplate which is electrically nonconductive;
   an indifferent electrode coupled with the baseplate for connecting with the body of the patient;
   a first connection part coupled with the baseplate and electrically connected with the indifferent electrode, the first connection part including a first connection socket; and
   a second connection part for connecting with the surgical electrode, the second connection part being coupled with the baseplate and spaced from the first connection part and the indifferent electrode, the second connection part including a second connection socket.

12. A connection element in accordance with claim 11 wherein the second connection socket is movably and displaceably guided in a channel in the baseplate.

13. A connection element in accordance with claim 12 wherein the channel is provided with an insertion opening for receiving an outer end piece of the surgical electrode into a region within the channel into which the second connection socket is to be inserted.

14. A connection element in accordance with claim 11 wherein the indifferent electrode is coupled to an underside of the baseplate, and the first connection part and second connection part are coupled to an upperside of the baseplate.

15. A connection element in accordance with claim 14 further comprising an electrically conductive member extending through the baseplate to connect the first connection part with the indifferent electrode.

* * * * *